United States Patent [19]

Weerda et al.

[11] Patent Number: 4,630,606

[45] Date of Patent: Dec. 23, 1986

[54] DEVICE FOR DETERMINING AND EVALUATING THE PRESSURE IN A BALLOON SLEEVE OF A CLOSED TRACHEAL TUBE

[75] Inventors: Hilko Weerda, Bad Krozingen; Peter Pedersen, Freiburg, both of Fed. Rep. of Germany

[73] Assignee: Drägerwerk AG, Fed. Rep. of Germany

[21] Appl. No.: 633,100

[22] Filed: Jul. 20, 1984

[30] Foreign Application Priority Data

Jul. 29, 1983 [DE] Fed. Rep. of Germany ....... 3327342

[51] Int. Cl.$^4$ ............................................. A61M 16/00
[52] U.S. Cl. .............................................. 128/207.14
[58] Field of Search ...................... 128/202.22, 207.15; 604/99, 100

[56] References Cited

U.S. PATENT DOCUMENTS

| | | | |
|---|---|---|---|
| 3,794,026 | 2/1974 | Jacobs | 128/202.22 |
| 3,848,591 | 11/1974 | Smythe et al. | 128/202.22 |
| 4,285,340 | 8/1981 | Gezari et al. | 128/207.15 |
| 4,414,982 | 11/1983 | Durkan | 128/202.22 |
| 4,535,766 | 8/1985 | Baum | 128/202.22 |

FOREIGN PATENT DOCUMENTS

| | | | |
|---|---|---|---|
| 8006749 | 7/1982 | Netherlands | 128/207.15 |
| 82/03014 | 8/1982 | World Int. Prop. O. | 128/207.15 |
| 2093218 | 8/1982 | United Kingdom | 128/207.15 |
| 2113101 | 8/1983 | United Kingdom | 128/207.15 |

Primary Examiner—Kyle L. Howell
Assistant Examiner—David Shay
Attorney, Agent, or Firm—McGlew and Tuttle

[57] ABSTRACT

A device and method for determining and acting upon the pressure in a balloon sleeve which closes a tracheal tube in the trachea of a patient comprises an inflation cannula which is connected to a pump and valve arrangement for inflating the sleeve. A pressure-to-voltage converter is connected to the cannula for sensing an instantaneous static pressure in the cannula. A differentiator is connected to the converter for differentiating the static pressure to produce a signal corresponding to pressure variations in the sleeve. The varying voltage corresponding to the pressure variations is then rectified and integrated to produce a signal that rises and falls with rising and falling frequency of pressure variations in the sleeve. If the rate becomes too high or too low, a signal is generated which is then again integrated to provide for transient unacceptable conditions. If upon integration it is found that the rate continues to remain too high or too low, the circuit for deflating the sleeve is activated to inflate the sleeve over the cannula. A respirator which is being used in conjunction with the tracheal tube can simultaneously be switched from a closed circuit ventilation mode to an open circuit ventilation mode. Warning lights and an audible alarm can be used in conjunction with limit value switches to provide visual and audible indications to an operator representing the pressure condition within the balloon sleeve.

17 Claims, 1 Drawing Figure

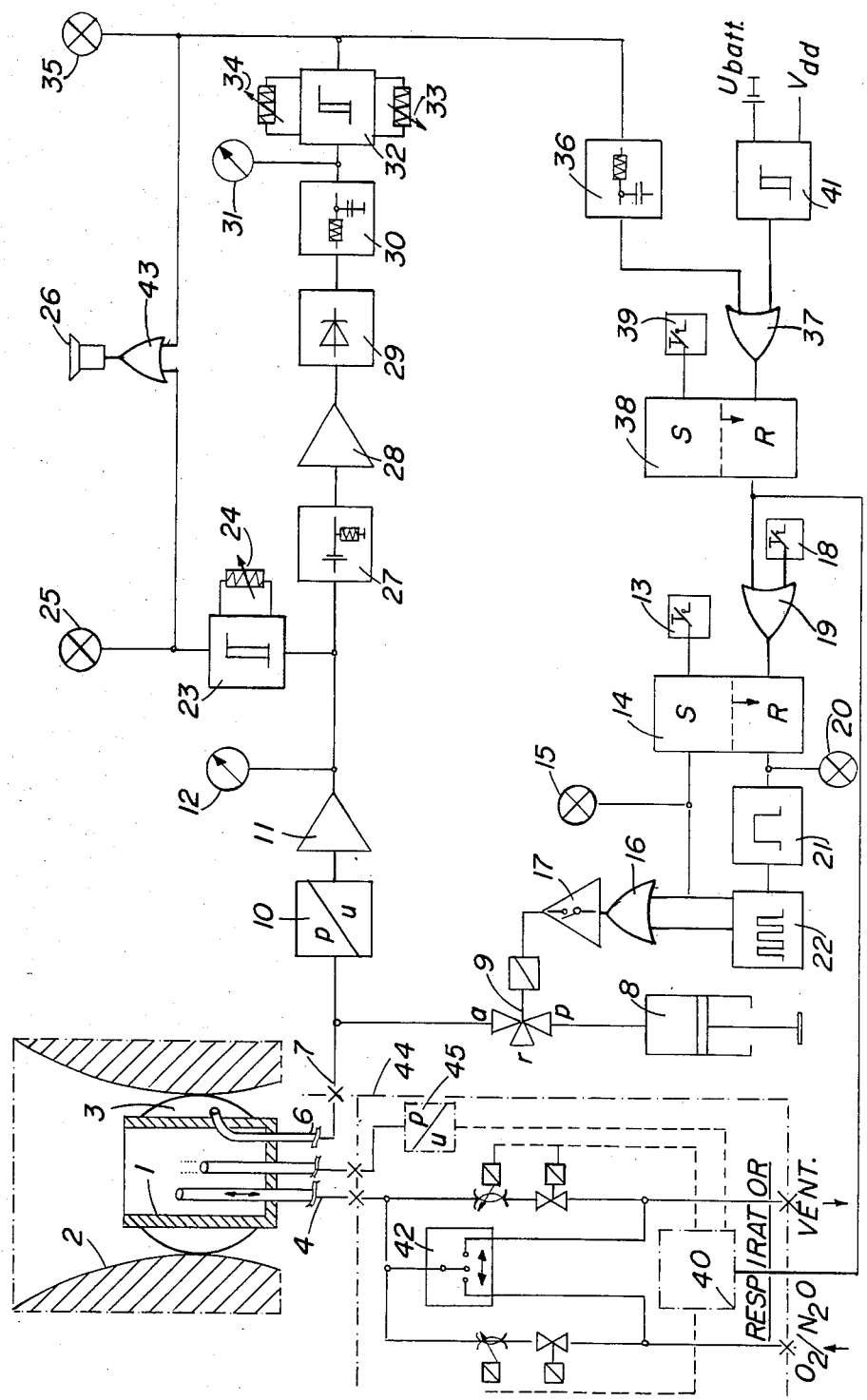

DEVICE FOR DETERMINING AND EVALUATING THE PRESSURE IN A BALLOON SLEEVE OF A CLOSED TRACHEAL TUBE

FIELD AND BACKGROUND OF THE INVENTION

The present invention relates in general to tracheal tubes for respirators and in particular to a new and useful device and method of evaluating the pressure in a balloon sleeve of the tracheal tube to determine if a ventilating operation utilizing the tracheal tube is valid.

While giving a patient artificial respiration by means of a closed tracheal tube such as the one disclosed in U.S. patent application Ser. No. 538,416 filed Oct. 3, 1983 (German application No. P 32 04 110.1-35), and a respirator which is designed for closed ventilation technique, the tracheal tube is applied in the trachea in a way such that its open end is directed to the carina and the lungs. By inflating a balloon sleeve embracing the tracheal tube, the tube is fixed to the wall of the trachea, and, along with the tube end at the side of the apparatus, seals the lungs against the larynx. With such a tube, the ventilation is effected through a thin flexible respiratory tube through which breathing gas is blown in and taken out by suction. A pressure measuring cannula, also extending into the tube, serves the purpose of measuring the intra-tracheal respiratory pressure and thus of controlling the respirator to produce in the lungs, the physiologically required breathing pattern.

If secretions from the tracheal and pulmonary region of the patient enter the open end of the pressure measuring cannula, clogging may be expected, and a risk arises of invalidating or stopping the pressure measuring operation. In such an event, the respiration control is unfavorably affected and the ventilation operation is not correct for the patient.

SUMMARY OF THE INVENTION

The present invention is directed to a device of the above mentioned kind for eliminating the risk of an incorrect artificial respiration due to a clogging of the pressure measuring cannula.

Accordingly an object of the present invention is to provide a device for determining and evaluating the pressure of a balloon sleeve on a closed tracheal tube which is equipped with a pressure gauge and which is connected to a cannula for inflating the balloon sleeve with a pressure converter and a control circuit for deblocking the balloon sleeve upon exceeding permissible pressure range limits, comprising the pressure converter being a pressure to voltage converter which, in order to monitor the static pressure, has its output applied to a first limit value switch which is responsive to a voltage drop below a prdetermined selectable threshold, and, in order to monitor a respiration pressure variation, has its output further applied to a differentiator which is connected, through a full wave rectifier and a first integrator, to a second selectable limit value switch which is responsive both to the exceeding of a predetermined upper limit value and the dropping below a predetermined lower limit value, the second settable limit value switch being connected through a second integrator to a control circuit for deblocking the balloon sleeve.

The inventive device makes it possible to detect a leak due to an unsatisfactory sealing of the sleeve, or a too high or too low ventilation pressure rate. The device responds to such faulty conditions by deblocking the balloon sleeve, and switching the respirator over to injection ventilation. Then, instead of a closed ventilation taking into account the actual value of the intra-tracheal pressure measured through the pressure measuring cannula, an open injection ventilation is obtained which does not take into account the tracheal pressure and the amounts of gas. After the trouble is remedied, the balloon sleeve can again be inflated and the respirator can be switched back into its "continual" mode of respiration.

The second integrator prevents a deblocking of the tracheal tube and switching over of the respirator which would be caused merely by temporary disturbances induced by the patents movements. Such disturbances of short duration are only indicated optically and acoustically, provided that they do not recur several times within the period predetermined by the time constant of the integrator.

A further object of the invention is to provide a method and device for determining and evaluating the pressure in a balloon sleeve of a closed tracheal tube which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWING

One embodiment of the invention is illustrated in the accompanying drawing. The single FIGURE is a block diagram of a device for determining and evaluating the pressure in an inflatable sleeve, and of a part of the respirator.

DESCRIPTION OF THE PREFERRED EMBODIMENT

The diagrammatically shown tracheal tube 1 for artificial respiration is inserted into a patient's trachea so as to be directed by its own end into the intra-tracheal space 2. By means of a balloon sleeve 3, which is a thin-walled soft rubber bag surrounding the tube and being radially secured thereto by its two ends to form an inflatable ring, tracheal tube 1 is fixed to the trachea wall by inflating the sleeve. This closes the tracheal tube 1 at the side of the device and sealingly separates the lungs from the larynx.

The ventilation is effected through a thin respiration cannula 4 extending within tracheal tube 1 to open into the free space at the end thereof. Cannula 4 is connected to a diagrammatically shown respirator 44. To control respirator 44, a pressure probe cannula 5 is provided, which also extends to the intratracheal space 2. In the respirator 44, pressure probe cannula 5 is connected to a pressure receiver 45 by which the intratracheal ventilation pressure is measured to control respirator 44 in a way such as to obtain in the lungs the physiologically needed breathing pattern.

The interior of balloon sleeve 3 is connected through an inflation cannula 6 to a connection 7 of a pump 8, which may be a syringe, equipped with a 3/2 directional solenoid valve 9. With valve 9 open, air may be pumped through connection 7 into balloon sleeve 3 until the sleeve tightly applies against the wall of the trachea, thus establishing a closed ventilation system. Connection 7 is thus connected to inflation recess for inflating balloon sleeve 3.

The pressure within balloon sleeve 3 is taken up by a pressure-to-voltage converter 10. The voltage corresponding to the instantaneous pressure is applied through an amplifier 11 to an indicator 12 where the static pressure within sleeve 3 can be read. This is to make sure that the pressure needed for applying sleeve 3 to the trachea wall is present.

To seal the pump off, solenoid valve 9 is closed by actuating a push button 13 by which an RS flip flop 14 is set. The S output of flip flop 14 is connected through an optical status indicator 15 and the first input of an OR gate 16. The output of OR gate 16 is applied to the input of a power switch 17 through which solenoid valve 9 is actuable. By actuating a push button 18 which is connected through an OR gate 19, to the reset input of flip flop 14, solenoid valve 9 can be opened, so that pressure is removed from sleeve 3 and a clear annular space is formed around the sleeve within the trachea. The inflation means 8,9 can thus be activated to deflate sleeve 3 by activating OR gate 19.

The resent output of flip flop 14 is connected to an optical status indicator 20, and to a one-shot multivibrator 21 through which, upon resetting flip flop 14, a pulse is produced having a duration of about one second. The output of one-shot multivibrator 21 is applied to a rectangular pulse generator 22 by which about 15 individual pulses are produced during the duration of the pulse produced by multivibrator 21 to control solenoid valve 9 through OR gate 16 and power switch 17. In this way, 3/2 directional valve 9 shortly opens and closes about 15 times, to let air escape from balloon sleeve 3 to the outside through its free R outlet.

During the time where, upon inflating balloon sleeve 3 and actuating push button 13, solenoid valve 9 is closed, the static pressure in balloon sleeve 3 is monitored by means of a first limit value switch 23 having its input connected to the output of amplifier 11. A threshold of zero to 100 millibar may be set as the minimum static pressure for switch 23, by means of a setting element 24. As soon as the pressure within sleeve 3, and thus the output voltage of amplifier 11, drops below the set threshold, limit value switch 23 actuates an optical indicator 25 and, in addition, through an OR gate 43, an acoustic indicator 26. The acoustic alarm and, simultaneously, the optical warning of indicator 25 make the operator aware of a low pressure in sleeve 3 which may be due to a leak in the sleeve.

The output of amplifier 11 is further connected to a differentiator 27 for separating ventilation pressure variations, which are superposed on the static pressure in the sleeve, from this static pressure and transmitting them to an amplifier 28. The output of amplifier 28 connects to the input of a full-wave rectifier 29 whose output voltage is applied to a first integrator 30. The pressure signals differentiated by means of differentiator 27 result at the output of first integrator 30 in a voltage having an average value which is higher, the more frequently and the faster the pressure in balloon sleeve 3 varies. An indicator 31 connected to the output of integrator 30, shows this average ventilation pressure rate PV.

The output of first integrator 30 is further connected to the input of a second limit value swtich 32 which is associated with a limit setting element 33 for the minimum ventilation pressure rate and a limit setting element 34 for the maximum ventilation pressure rate. Upon exceeding one of the respective values set by means of element 33 and 34, second limit value switch 32 responds, to cause a warning through an optical indicator 35 and the already mentioned acoustical indicator 26.

The output signal of second limit value switch 32 further passes to a second integrator 36. As soon as the frequency of duration of the signals delivered by the second limit value switch 32 exceeds a value depending on the time constant of second integrator 36, the integrator signal enables an OR gate 37 behaving as a Schmitt trigger. In this way, upon exceeding a preset warning time, the output signal of OR gate 37 causes resetting of a second RS flip flop 38 which has been set for continual ventilation by means of a push button 39.

With short disturbances, optical warning indicator 38 lights up shortly, so that flip flop 38 is not reset. Only if the disturbance is long enough to exceed the warning time predetermined through second integrator 36, flip flop 38 is reset, so that, through OR gate 19, first flip flop 14 is also reset, which results in causing balloon sleeve 3 to deflate and clear the passage.

As may be learned from the schematic drawing, the warning by resetting flip flop 38 is also passed to a control 40 of respirator 44, to effect a switching in respirator operation for control purposes, from the continual ventilation under actual values of the intertracheal pressure and inspiration flow as the control inputs, to an operating mode of artificial ventilation by respirator 44, controlled by present desired values, without using the tracheal pressure and/or the gas flow as measuring or controlling quantities. These two operations and the parts of the respirator 44 to achieve them, are well known in the field and additional details will not be provided here.

After this switching of respirator 44, the respiration acts as an open injection ventilation, with tracheal tube 1 no longer being tightly seated in the trachea. The excess pressures or underpressures produced during this ventilation are equalized by the annular space between the trachea and tracheal tube 1.

Upon eliminating the disturbance which has caused the switching, balloon sleeve 3 can be inflated again and respirator 44 can be switched back to the "continual ventilation" mode.

To detect a power failure, a power monitoring circuit 41 is provided. In the case of such a failure, circuit 41 releases an acoustic warning signal and causes resetting of first flip flop 38, so that balloon sleeve 3 is vented and respirator 44 is switched over. A further consequence of a power failure is that respirator 44 stops operating, so that a manually operable valve provided for this event must effect the ventilation.

The breathing gas is then supplied and taken off by a hand-operated two-way valve 42 with an inactive central position, until the fault is remedied or another respirator is connected.

While a specific embodiment of the invention has been shown and described in detail to illustrate the application of the principles of the invention, it will be understood that the invention may be embodied otherwise without departing from such principles.

What is claimed is:

1. A device for determining and acting upon the pressure in a balloon sleeve of a closed tracheal tube, with inflation means connected to the sleeve for inflating and deflating the sleeve, comprising:
- a tracheal tube;
- a balloon sleeve surrounding said tube;
- inflation means, connected to said sleeve, for inflating said sleeve;
- deflation means connected to the inflation means for deflating the sleeve;
- a cannula connected to the sleeve and to the inflation means for inflating the sleeve;
- a pressure-to-voltage converter connected to said cannula for generating a first voltage signal corresponding to an instantaneous static pressure in the sleeve; and
- voltage signal processing means connected between said converter and said deflating means for producing a deflation signal when a frequency of variations of pressure in the sleeve is out of a selected range of frequencies for a selected period of time, said deflation signal being applied to said deflation means for deflating the sleeve.

2. A device according to claim 1 wherein said voltage signal processing means comprises:
- a differentiator connected to said converter for differentiating said first voltage signal;
- a full-wave rectifier connected to said differentiator for rectifying the differentiated first voltage signal to generate a second voltage signal corresponding to ventilation pressure variations in the sleeve;
- a first integrator connected to said rectifier for integrating the second voltage signal to generate a third voltage signal corresponding to a frequency of ventilation pressure variations in the sleeve;
- a limit value switch having an upper frequency limit and a lower frequency limit connected to said first integrator for generating a fourth voltage signal when the frequency of ventilation pressure variations rises above the upper frequency limit or falls below the lower frequency limit; and
- a second integrator connected to said limit value switch for integrating said fourth voltage signal to generate the deflation signal.

3. A device according to claim 2, wherein said voltage signal processing means further includes a first limit value switch connected to said pressure-to-voltage converter for receiving said first voltage signal, a visual indicator connected to said first limit value switch for activation when said first voltage signal falls below a selected value, said first mentioned limit value switch forming a second limit value switch.

4. A device according to claim 3, including a second indicator connected to said second limit value switch for generating a visual indication upon the occurrence of said fourth voltage signal, an OR gate having a first input connected to said first limit value switch and a second input connected to said second limit value switch, and an audible alarm connected to said OR gate for activation upon the occurrence of said fourth voltage signal or the occurrence of an output from said first limit value switch.

5. A device according to claim 3, including at least one limit value setting element connected to said first limit value switch and at least two limit value setting elements connected to said second limit value switches for setting desired limiting values on said first and second limit value switches.

6. A device according to claim 2, including an indicator connected to said converter for providing a visual indication of said first voltage signal corresponding to a static pressure in the sleeve and a further indicator connected to said first integrator for providing an indication of the third voltage signal corresponding to the frequency ventilation pressure variations in the sleeve.

7. A device according to claim 1, wherein inflation means includes a controllable valve having an open position for deflating the sleeve and a closed position for inflating the sleeve, said deflation means comprising a first flip flop having a first input activatable to close the shut-off valve and a second input activatable to open the shut-off valve, a first push button connected to said first input of said first flip flop for manually closing the valve, a second flip flop connected to said second input of said first flip flop, said second flip flop having a first input activatable to keep said valve closed and a second input activatable to activate said first flip flop to open said valve, a second push button connected to said first input of said second flip flop for manually keeping said valve closed, said second input of said second flip flop being connected to said voltage signal processing means for responding to said deflation signal to open said valve.

8. A device according to claim 2, wherein inflation means includes a controllable valve having an open position for deflating the sleeve and a closed position for inflating the sleeve, said deflation means comprising a first flip flop having a first input activatable to close the shut-off valve, and a second input activatable to open the shut-off valve, a first push button connected to said first input of said first flip flop for manually closing the valve, a second flip flop connected to said second input of said first flip flop, said second flip flop having a first input activatable to keep said valve closed and a second input activatable to activate said first flip flop to open said valve, a second push button connected to said first input of said second flip flop for manually keeping said valve closed, said second input of said second flip flop being connected to said voltage signal processing means for responding to said deflation signal to open said valve.

9. A device according to claim 8, including an OR gate having an output connected to said second input of said second flip flop, a first input connected to an output of said second integrator and a second input connected to power monitoring means which receive power for said device, for activating said second input of said second flip flop upon a power failure.

10. A device according to claim 9, including a second OR gate having an output connected to said second input of said first flip flop, a first input connected to an output of said second flip flop and a second input, a third push button connected to said second input of said second OR gate for manually activating said second input of said first flip flop to open said valve.

11. A device according to claim 10, including an optical status indicator connected to said first flip flop for indicating an open and a closed condition of said valve.

12. A device according to claim 2, including a respirator having a respiration cannula connected to said tracheal tube for supplying discharging respiratory gas, switch means in said respirator for switching said respirator from a closed ventilation mode to an open ventilation mode, said signal processing means connected to said switch means for switching said respirator to an open ventilation mode upon the occurrence of said deflation signal.

13. A device according to claim 10, including a respirator having a respiration cannula connected to said tracheal tube for supplying and discharging respiratory gas, said respirator having switching means for switching said respirator from a closed ventilation mode to an open ventilation mode, said second flip flop having an output connected to said switching means for switching said respirator to the open ventilation mode when said second input of said second flip flop is activated.

14. A method of determining and acting upon the pressure in a balloon sleeve of a closed tracheal tube having inflation means for inflating the sleeve, comprising:

inflating the sleeve;

monitoring the pressure in the sleeve;

converting the monitored pressure to a corresponding voltage signal;

differentiating the voltage signal and rectifying differentiated voltage signal to obtain a further voltage signal which corresponds to a ventilation pressure variation in the sleeve;

integrating the further signal to produce a third voltage signal which corresponds to the frequency of ventilation pressure variations in the sleeve;

generating a fourth voltage signal when the frequency rises above or falls below set limits for the frequency of pressure variations in the sleeve; and deflating the sleeve upon the occurrence of the fourth voltage signal.

15. A method according to claim 14, including integrating the fourth voltage signal to produce a signal for deflating the sleeve only when the frequency is above or below selected values for a selected period of time.

16. A method according to claim 15, including ventilating the tracheal tube using a respirator having a closed ventilation mode and an open ventilation mode, using the respirator in the closed ventilation mode with the sleeve inflated and, supplying a signal to the respirator for switching the respirator to the open ventilation mode when the second integration produces a signal indicating the frequency is above or below its selected values for the selected period of time.

17. A method according to claim 16, including indicating the static pressure in the sleeve, indicating the frequency of pressure variations in the sleeve and activating a warning when the static pressure falls below a selected limit or when the frequency rises above or falls below its selected limits.

* * * * *